(12) United States Patent
Deckert et al.

(10) Patent No.: US 8,697,921 B2
(45) Date of Patent: Apr. 15, 2014

(54) PROCESS FOR PURIFYING WASTEWATERS FROM THE WORKUP OF CRUDE AROMATIC NITRO COMPOUNDS

(75) Inventors: Petra Deckert, Bammental (DE); Leo Denissen, Brasschaat (BE); Bart Van De Voorde, Antwerpen (BE); Julia Leschinski, Ixelles (BE); Stefan Robert Deibel, Hoeilaart (BE); Matthias Fankhaenel, Dackenheim (DE); Samuel Neto, Brussels (BE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/569,806

(22) Filed: Aug. 8, 2012

(65) Prior Publication Data

US 2013/0041189 A1 Feb. 14, 2013

Related U.S. Application Data

(60) Provisional application No. 61/521,390, filed on Aug. 9, 2011.

(51) Int. Cl.
*C07B 41/00* (2006.01)
(52) U.S. Cl.
USPC .......................................................... 568/950
(58) Field of Classification Search
USPC .......................................................... 568/950
See application file for complete search history.

(56) References Cited

U.S. PATENT DOCUMENTS

| | | | |
|---|---|---|---|
| 2012/0136181 A1* | 5/2012 | Berretia | 568/934 |
| 2012/0157722 A1 | 6/2012 | Denissen et al. | |
| 2012/0205308 A1 | 8/2012 | Leschinski et al. | |

FOREIGN PATENT DOCUMENTS

| | | |
|---|---|---|
| EP | 0 378 994 A1 | 7/1990 |
| EP | 0 436 443 A2 | 7/1991 |
| EP | 0 953 546 A2 | 11/1999 |
| EP | 1 593 654 A1 | 11/2005 |
| WO | WO 2009/027416 A1 | 3/2009 |
| WO | WO 2011/021057 A1 | 2/2011 |
| WO | WO 2011/023638 A1 | 3/2011 |
| WO | WO 2012/025393 A1 | 3/2012 |
| WO | WO 2013/020798 A1 | 2/2013 |

OTHER PUBLICATIONS

U.S. Appl. No. 13/759,466, filed Feb. 5, 2013, Raichle, et al.

* cited by examiner

*Primary Examiner* — Jafar Parsa
(74) *Attorney, Agent, or Firm* — Oblon, Spivak, McClelland, Maier & Neustadt, L.L.P.

(57) ABSTRACT

The invention relates to a process for purifying crude aromatic nitro compounds which originate from the nitration of aromatic compounds, comprising the single or multiple performance of the following wash stage (a):

(a) contacting the crude aromatic nitro compound (N-in) with an aqueous phase (W-res) and then separating the phases to obtain an organic phase (N-res) and an aqueous phase (W-res), wherein at least one demulsifier (D) is present in one or more of the wash stages (a).

19 Claims, No Drawings

PROCESS FOR PURIFYING WASTEWATERS FROM THE WORKUP OF CRUDE AROMATIC NITRO COMPOUNDS

The invention relates to a process for purifying crude aromatic nitro compounds which originate from the nitration of aromatic compounds, comprising the single or multiple performance of the following wash stage (a):
(a) contacting the crude aromatic nitro compound (N-in) with an aqueous phase (W-in) and then separating the phases to obtain an organic phase (N-res) and an aqueous phase (W-res),
wherein at least one demulsifier (D) is present in one or more of the wash stages (a).

Aromatic nitro compounds, especially mononitrobenzene, are prepared in commercial processes typically by direct nitration of benzene with a mixture of nitric acid and sulfuric acid, known as nitrating acid. This reaction is a biphasic reaction, the reaction rate of which is determined by the mass transfer between the phases and by the chemical kinetics. Of particular industrial significance are continuous processes, and the adiabatic reaction regime has gained particular significance in recent times.

The reaction product (crude product) obtained from the nitration of the aromatic starting compound, especially mononitrobenzene, is initially obtained as a biphasic mixture, the organic phase comprising, as well as the organic nitro compound, further organic by-products and unconverted organic starting materials. In addition to organic constituents, for example mononitrobenzene and benzene, the aqueous phase of course comprises unconsumed nitrating acid. According to the prior art, the acid-containing aqueous phase is typically concentrated in an acid concentrator (sulfuric acid concentration, SAC) and recycled back into the nitrating reaction.

The organic phase obtained from the nitration, referred to hereinafter as crude aromatic nitro compound (N-in), is contaminated both with organic secondary components, for example dinitrobenzene, benzene, nitrophenols, and with nitrating acid, and requires a multistage workup which has to meet high demands with regard to energy and process costs, yield and purification of waste streams from an environmental standpoint. Processes for working up crude aromatic nitro compounds are known from the prior art.

Typically, the removal of the crude aromatic nitro compound, especially crude mononitrobenzene, from the acid-containing aqueous phase is followed by at least one washing operation to wash the crude aromatic nitro compound with water or an aqueous solution.

The aqueous phase which results from the aforementioned washing operation (referred to hereinafter as wastewater) comprises, as well as water and salts, also organic compounds such as mononitrobenzene, dinitrobenzene, nitrophenols (mono- and polynitrated phenols) and benzene.

The required depletion of the undesired organic constituents from the wastewater before the introduction thereof into a biological wastewater treatment (water treatment plant) constitutes a significant proportion of the capital costs in the installation of plants for preparation of aromatic nitro compounds.

EP 1 593 654 A1 describes a process for working up alkaline wastewaters which arise in the washing of crude nitrobenzene, the crude nitrobenzene being prepared by adiabatic nitration of benzene with nitrating acid and then being washed in an acidic wash and then in an alkaline wash to obtain an alkaline wastewater comprising benzene in concentrations of 100 to 3000 ppm and nitrobenzene in concentrations of 1000 to 10 000 ppm. Benzene and/or nitrobenzene not present in dissolved form are then separated out of the alkaline wastewater, and then residual benzene and/or nitrobenzene are optionally removed from the alkaline wastewater by stripping. The alkaline wastewater is subsequently heated with exclusion of oxygen to temperatures of 150 to 500° C. under elevated pressure. Acidic wastewaters according to the prior art are, however, disadvantageous in respect of the further workup. They generally comprise constituents which have to be removed with additional complexity before supply to a biological wastewater treatment. Acidic wastewaters often additionally lead to corrosion problems in downstream purification stages, which can be remedied only by means of additional technical complexity.

Wastewater obtained according to the prior art additionally comprises, in all stages, nitrophenoxides or nitrophenols, such that all wastewaters have to be supplied to a complex and expensive thermolytic decomposition. It is thus desirable to provide a process for purifying crude aromatic nitro compounds, which supplies at most a portion of the wastewaters to a thermolytic water treatment.

The organic constituents can be removed from the wastewater, for example, by a one-stage or multistage extraction with benzene. One known process is the one-stage or multistage stripping of the organic constituents with steam, which especially removes low-boiling organic impurities, and subsequent thermolytic or oxidative decomposition of organic constituents still present in the resulting wastewater.

For instance, EP 0 953 546 A2 describes a process for degrading aromatic nitro compounds in wastewaters by heating the wastewater to temperatures of 150 to 350° C. under a pressure of 10 to 300 bar. EP 0 953 546 A2 states that the wastewaters thus treated can be purified biologically.

However, the decomposition of nitro compounds in aqueous wastewaters according to the prior art forms ammonia, which has adverse effects in biological water treatment plants. $NH_3$-containing wastewater supplied to a biological wastewater treatment first has to be subjected to a nitrification. Nitrification refers to the bacterial oxidation of ammonia ($NH_3$) to nitrate ($NO_3^-$). It consists of two coupled process components: in the first part, ammonia is oxidized to nitrite, which is oxidized in the second process component to nitrate. Nitrification is associated with production of acid ($H^+$ formation); the pH is lowered unless the acid formed is neutralized, for instance by reaction with calcium carbonate ($CaCO_3$). The acid formed is a burden on the buffer capacity of the water and can acidify the water or the soil. Since nitrifying microorganisms metabolize only in the neutral to slightly alkaline range, the acidification can prevent the complete conversion of the ammonium/ammonia, which is toxic to fish, in wastewater treatment plants (autoinhibition).

The nitrate formed is subsequently subjected, in a further stage of the biological wastewater treatment, to a denitrification to form $N_2$. Denitrification is understood to mean the conversion of the nitrogen bound within the nitrate ($NO_3^-$) to molecular nitrogen ($N_2$) by particular heterotropic and some autotropic bacteria, which are accordingly referred to as denitrificants.

Accordingly, the wastewater which arises according to the prior art can be sent to the biological wastewater treatment only after complex processing to remove all nitrophenols.

Furthermore, the wash stages known from the prior art are unsatisfactory: the phase separation is not sufficiently rapid and/or is incomplete, and so undesirable constituents remain in the respective phase.

It was thus an object of the present invention to provide a process for purifying crude products from the nitration of aromatic compounds which has the aforementioned disadvantages only to a lesser degree, if at all. More particularly, the wash stages were to be performable very quickly. The phase separation was to be very substantially complete within a given time.

In addition, the process should produce at least some wastewaters which, optionally after stripping and optional removal of ammonia, can be supplied directly to a biological wastewater treatment, specifically with omission of any thermal and/or oxidative workup. The total amount of wastewater produced should be at a minimum.

The aforementioned objects are achieved by the process according to the invention. Preferred embodiments can be inferred from the claims and the description which follows. Combinations of preferred embodiments do not leave the scope of the present invention, especially in respect of combinations of preferred embodiments of the different stages of the process according to the invention.

According to the invention, the process comprises the single or multiple performance of the following wash stage (a):

(a) contacting the crude aromatic nitro compound (N-in) with an aqueous phase (W-in) and then separating the phases to obtain an organic phase (N-res) and an aqueous phase (W-res), wherein at least one demulsifier (D) is present in one or more of the wash stages (a).

The terms "washing" and "wash stage" in the context of the present invention refer to the contacting of an organic phase with an aqueous phase, in the course of which at least one constituent of the organic phase is at least partly transferred to the aqueous phase, including the subsequent phase separation. The washing of organic phases and the subsequent removal of the phases is known per se to those skilled in the art and can be effected in apparatuses known per se such as mixing-removal units (mixing unit followed by removal unit) or extractors, for example extraction columns.

Multiple performance (synonym: multistage performance) is understood to mean that every successive stage in the aqueous phase used (W-in) differs from the preceding stage. It is additionally also possible to perform each individual stage in one step or in several sub-steps (repetitions). Performance of one stage in several sub-steps is understood to mean that the sequence of contacting-phase separation is performed several times in succession with one aqueous phase, for example W1-in. It is preferable here to conduct the aqueous phase used in countercurrent to the stream of the crude aromatic nitro compound N-in, which means that, in the case of performance in two sub-steps, the aqueous phase which is the result of the second sub-step is contacted in the first sub-step with the crude aromatic nitro compound N1-in used. This is explained in detail below.

In the case of multiple performance of wash stage (a), which is preferable, these stages are referred to hereinafter as wash stages (a1), (a2), etc. in the sequence of their performance. The wash stage comprising the contacting of the crude aromatic nitro compound (N-in) with an aqueous phase (W-res) and subsequent separation of the phases to obtain an organic phase (N-res) and an aqueous phase (W-res) is correspondingly performed multiply; the corresponding phases are referred to as W1-in, W2-in, W1-res, W2-res, N1-in, N2-in, N2-in, N2-res, etc.

According to the invention, at least one demulsifier is present in at least one wash stage (a). In the case of two-stage performance, this means that at least one demulsifier (D) is present in stage (a1) or in stage (a2) or in both stages (a1) and (a2).

If a demulsifier (D) is used in several stages, for example in stage (a1) and in stage (a2), these demulsifiers may be the same or different. In the case of multistage performance, especially in the case of performance in two stages, the demulsifier(s) used in stage (a1) is preferably the same as used in stage (a2).

The term "demulsifier" in the context of the present invention is used synonymously with "phase separator", and refers to an assistant which accelerates the separation of the organic phase and the aqueous phase and/or improves the quality of the phase separation. Without wishing to impose a restriction, it is thought that the demulsifiers act as an interface-active substance and thus influence the rate of formation of an altered, i.e. reduced, interface between aqueous and organic phase. Demulsifiers are also referred to in the prior art as emulsion splitters or emulsion separators. Although demulsifiers known from the prior art are also useful in principle for the present invention, this does not mean that the aqueous phases and organic phases form a (stable) emulsion in all cases.

The expression "in the presence of at least one demulsifier" means that at least one demulsifier is present in at least one sub-step of the particular stage, for example stage (a1) and/or (a2). It is preferable when the demulsifier is present in the respective stage in the course of mixing of the organic phase (N-in) and the aqueous phase (W-in), since it is thus possible to establish a good distribution at the interface between the two phases. When a mixing apparatus and then a phase separation apparatus are used in the particular stage or in the particular sub-step (contacting-phase separation), the demulsifier(s) is/are thus preferably added in the mixing apparatus, since the phase separation apparatus alone does not give sufficient mixing.

The demulsifiers (D) used are preferably amphiphilic compounds. Amphiphilic compounds are compounds having at least one hydrophilic and at least one hydrophobic molecular section, and a section may be a functional group, a comonomer, an end group or a block of a block copolymer. Corresponding amphiphilic compounds are known to those skilled in the art. Suitable demulsifiers (D) may have different ways of working. More particularly, the demulsifiers (D) may stabilize the reverse dispersion direction, alter wetting properties of solids or displace other compounds which work as emulsifiers from the interface but have lesser stabilizing action than these demulsifiers.

In the context of the present invention, the demulsifiers (D) are used preferably in an amount of 0.1 to 1000 ppm, especially of 1 to 200 ppm, more preferably of 1 to 100 ppm, most preferably of 2 to 60 ppm, based in each case on the total weight of the aqueous phase used in the particular stage. In the case of two-stage performance, the amount of demulsifier in ppm relates to the weight W1-in and/or W2-in. The weight of the demulsifier here forms part of the total weight of the aqueous phase W-in used.

Amphiphilic anionic copolymers are preferred as demulsifiers (D). The content of monomer units which comprise anionic groups is preferably from 0.1 to 5% by weight, based on the weight of the copolymer. The anionic groups used are preferably carboxylate groups.

The demulsifiers (D) are more preferably essentially water-soluble, especially water-soluble. Demulsifiers (D) are essentially water-soluble when they are either completely water-soluble or have at most slight cloudiness in a proportion of 10% by weight in distilled water. Use of water-soluble demulsifiers prevents them from getting into the product. Instead, demulsifiers are then removed with the aqueous phase in the process according to the invention.

Preferred ampiphilic anionic copolymers have a number-average molecular weight of 5000 to 20 000 g/mol. Preferred amphiphilic anionic copolymers also have a K value to ISO 1628-1 (1% by weight of dry substance in distilled water) of 25 to 50.

Corresponding amphiphilic anionic copolymers are known per se to those skilled in the art. They are obtainable especially by copolymerization of acrylic acid and/or maleic acid with hydrophilic monomer units, for example vinyl monomers or olefins.

The selection of suitable demulsifiers (D) is made by the person skilled in the art on the basis of the following profile of properties: suitable demulsifiers are effective in low concentrations, especially in the range from 1 to 100 ppm; they are chemically inert; they are not disruptive in the product, for example because they are of no relevance for wastewater, or do not get into it.

Copolymers comprising maleic acid units, especially copolymers based on maleic acid and at least one olefin, are particularly preferred as demulsifiers (D).

The present process is especially suitable for the workup of wastewaters which arise in the purification of crude mononitrobenzene which has been obtained by nitrating benzene. For this reason, the process is illustrated by way of example with reference to this specific purification. However, the person skilled in the art can apply the embodiments mentioned without difficulty to other aromatic compounds than benzene or to products other than mononitrobenzene.

The crude aromatic nitro compounds which can be purified by the process according to the invention preferably originate from nitration plants for nitration of aromatic compounds, for example nitrobenzene plants, dinitrotoluene plants and nitrotoluene and nitroxylene plants. The crude aromatic nitro compound is preferably crude mononitrobenzene which is obtained by nitrating benzene.

The nitration of aromatic starting compounds (especially benzene) to aromatic nitro compounds (especially mononitrobenzene) can be effected by the processes known from the prior art. Suitable processes are described, for example, in EP 043 6 443 A2 and in Kirk-Othmer, Encyclopedia of Chemical Technology, "Nitrobenzene and Nitrotoluenes", published online on Oct. 14, 2005.

Once the liquid products have left the nitration reactor, a phase separation is first undertaken, in which an organic phase comprising principally mononitrobenzene, and also unconverted benzene and traces of organic secondary components, especially nitrophenols, is obtained. The aqueous phase comprises essentially water and sulfuric acid. After the removal of the water of reaction, the aqueous phase is typically sent back to the process, while the organic product of value phase (the crude aromatic nitro compound) is treated in accordance with the invention. More particularly, this removes nitrophenols.

In a preferred embodiment, the process for purifying crude aromatic nitro compounds which originate from the nitration of aromatic compounds comprises the following wash stages (a1) and (a2), where each of stages (a1) and (a2) may be performed once or more than once in succession:

(a1) contacting the crude aromatic nitro compound (N1-in) with a first aqueous phase (W1-in) comprising at least one base (B) and then separating the phases to obtain an organic phase (N1-res) and an aqueous phase (W1-res); and then (a2) contacting the organic phase (N1-res) obtained in stage (a1) with a second aqueous phase (W2-in) and then separating the phases to obtain a purified organic phase (N2-res) and at least one aqueous phase (W2-res), the aqueous phase used (W2-in) having a pH of 6 to 9.

Wash stages (a1) and (a2) of the preferred embodiment are explained in detail hereinafter. It is, however, clear to the person skilled in the art that he can also employ the preferred embodiments explained hereinafter to embodiments with fewer or more than two wash stages, for example three.

Wash Stage (a1)

The wash stage (a1) explained hereinafter is also referred to as the alkaline wash. The crude aromatic nitro compound N1-in used in stage (a1) is also referred to as organic phase N1-in. Wash stage (a1) can, in accordance with the invention, be performed twice or more in succession.

In this preferred embodiment, according to wash stage (a1), the crude aromatic nitro compound (N1-in) is contacted with a first aqueous phase (W1-in) which comprises at least one base (B) and then the phases are separated to obtain an organic phase (N1-res) and an aqueous phase (W1-res).

Apparatuses for performance of stage (a1) are known to those skilled in the art. Preferably, in a first apparatus, a mixing apparatus, intensive mixing of the two phases is first conducted in order to accelerate the formation of phenoxides and the transfer of phenoxides from the organic phase (N1-in) to the aqueous phase (W1-in). It has been found to be advantageous to perform the mixing while stirring. Subsequently, preferably in a second apparatus, a phase separation apparatus, the two phases are separated. However, it is also possible to combine the two apparatuses mentioned in one apparatus. Useful phase separation apparatuses in principle include all apparatuses known for this purpose to those skilled in the art, especially settlers and centrifuges.

The pH of the first aqueous phase (W1-in) comprising at least one base (B) is, in the form used, preferably from 9 to 14, more preferably from 9 to 12.5, especially from 9.5 to 11.

Suitable bases (B) are especially ammonia and alkali metal hydroxides. Alkali metal hydroxides are preferred, especially lithium hydroxide, sodium hydroxide, potassium hydroxide and/or rubidium hydroxide. Sodium hydroxide is particularly preferred as a base (B).

The base (B) is preferably added in the form of aqueous solutions of the base, which means that at least portions of the aqueous solution used in stage (a) comprise said base (B). The base (B) preferably added in excess produces phenoxides from the phenolic organic compounds and neutralizes the nitrating acid present in the organic phase to form soluble salts. The resulting pH of the wastewater (W1-res) is preferably from 8 to 14, more preferably 9 to 13, especially 9 to 11.

As already detailed above, the wash stage (a1) can be performed twice or more in succession, preferably in two or three sub-steps (repetitions), preferably in a sequence of mixing and phase separation apparatuses. It is advantageous to conduct the aqueous phase (W1-in) in countercurrent to the organic phase (N1-in) in the course of wash stage (a1). As a result, prepurified organic phase comes into contact with aqueous phase (W1-in) which has yet to pass through any sub-step. This allows the phenoxides to be extracted to a particularly complete degree and transferred to the aqueous phase.

In principle, numerous aqueous phases (W1-in) are options, provided that they meet the requirements in respect of base (B). Preference is given to using nitrophenol-containing wastewaters from the workup of the nitrating acid as the aqueous phase. This makes it possible to combine various nitrophenol-containing wastewaters and thus to minimize the amount of wastewater from which nitrophenols have to be removed by thermolysis or ozonolysis.

The wastewater resulting from stage (a1) typically comprises, in addition to water, also residual amounts of benzene and nitrobenzene, and nitrophenols. The wastewater resulting from stage (a) typically comprises benzene in concentrations of 10 to 3000 ppm, preferably of 100 to 1000 ppm, and nitrobenzene in concentrations of 500 to 10000 ppm, preferably of 1200 to 8000 ppm. The wastewater also typically comprises nitrophenoxides in a concentration of 1000 to 20000 ppm, especially 2000 to 8000 ppm. In the context of the present invention, the unit ppm always relates to parts by weight.

Particular examples include the following nitrophenols, which may also be in the form of the water-soluble salts thereof: mono-, di- and trinitrophenols, mono-, di- and trinitrocresols, mono-, di- and trinitroresorcinols, mono-, di- and trixylenols.

Wash Stage (a2)

In the preferred embodiment, according to wash stage (a2), the organic phase (N1-res) obtained in stage (a1) is subsequently contacted with a second aqueous phase (W2-in) and then the phases are separated to obtain a purified organic phase (N2-res) and at least one aqueous phase (W2-res), the aqueous phase (W2-in) used having a pH of 6 to 9. Stage (a2) is preferably performed in the absence of a base (B) in the aqueous phase (W2-in). This wash stage (a2) repeated once or more than once sequentially is also referred to as the neutral wash.

Apparatuses for performance of stage (a2) are known to those skilled in the art. It is possible to use the same apparatuses as in stage (a1). Preferably, in a first apparatus, a mixing apparatus, intensive mixing of the two phases is first conducted in order to accelerate the transfer of salts from the organic phase (N2-in) to the aqueous phase (W2-in). It has been found to be advantageous to perform the mixing while stirring. Subsequently, preferably in a second apparatus, a phase separation apparatus, the two phases are separated. However, it is also possible to combine the two apparatuses mentioned in one apparatus.

As already detailed above, the wash stage (a2) can be performed twice or more in succession, preferably in one or two sub-steps (repetitions), preferably in a sequence of mixing and phase separation apparatuses. It is advantageous to conduct the aqueous phase (W2-in) in countercurrent to the organic phase (N2-in) in the course of wash stage (a2). As a result, the purified organic phase (N2-res) comes into contact with aqueous phase which has yet to pass through any sub-step. This allows inorganic salts to be extracted to a particularly complete degree and transferred to the aqueous phase.

In a preferred embodiment, stage (a2) is performed in two sub-steps (repetitions) and the aqueous phase (W2-in) used is conducted in countercurrent to the organic phase (N2-in) in the course of the wash stage (a2).

In principle, numerous aqueous phases (W2-in) are options, provided that they meet the inventive requirements. Preference is given to using wastewaters which are essentially free of nitrophenols. An aqueous phase is referred to as being essentially free of nitrophenols when it comprises not more than 30 ppm, especially not more than 20 ppm, of nitrophenols. More preferably, the aqueous phase W2-in has a content of nitrophenols of not more than 5 ppm, especially not more than 3 ppm. Accordingly, preference is given to using wastewaters from a different production process which are essentially free of nitrophenols. The aqueous phase (W2-in) used is preferably a wastewater which results from the hydrogenation of mononitrobenzene for aniline production. This makes it possible to work up several wastewaters from different production processes together and thus inexpensively. This reduces the total amount of wastewater in a combined process.

In a preferred embodiment, which can be implemented independently of the aforementioned preferred embodiments, after stage (a) and before performance of stage (b) or stage (c), benzene and/or nitrobenzene still present in undissolved form are removed from the wastewater.

The nitrobenzene present in undissolved form can be removed by means of separators, settling vessels or other phase separation apparatuses. Preference is given to using a settling vessel. This removal can alternatively be performed in the form of an extraction, as described in WO 2009/027416. The benzene and/or nitrobenzene thus removed is then preferably sent back to the nitration process or the crude nitrobenzene.

The aqueous phase W2-res resulting from wash stage (a2) preferably has a content of nitrophenols of not more than 20 ppm, especially of 0.001 to 20 ppm. More preferably, the content of nitrophenols in W2-res is not more than 10 ppm, especially from 0.001 to 10 ppm, most preferably not more than 5 ppm, especially from 0.001 to 5 ppm.

In a preferred embodiment, the process according to the invention comprises further stages for workup of the aqueous phases W1-res and W2-res resulting from the process.

In a preferred embodiment, which can be implemented independently of the aforementioned preferred embodiments, the aqueous phase (W1-res) is subjected to the following further workup stages:

(b) optional removal of organic constituents from at least a portion of the aqueous phase (W1-res) obtained in stage (a) by stripping, preferably with steam,
(c) removal of organic compounds from at least a portion of the aqueous phase (W1-res) resulting from stage (a) or stage (b) by thermal and/or oxidative degradation,
(d) distillative depletion of ammonia from at least a portion of the aqueous phase resulting from stage (c), and
(e) optional supply of at least a portion of the aqueous phase resulting from stage (d) to a biological wastewater treatment.

In another preferred embodiment, which can be implemented independently of the aforementioned preferred embodiment, provided that the resulting aqueous phases are not contaminated, the aqueous phase (W2-res) is subjected to the following further workup stages:

(b) optional removal of organic constituents from at least a portion of the aqueous phase (W2-res) obtained in stage (a) by stripping, preferably with steam,
(d) optional distillative depletion of ammonia from at least a portion of the aqueous phase(s) resulting from stage (c), and
(e) optional supply of at least a portion of the aqueous phase resulting from stage (d) to a biological wastewater treatment, The aforementioned workup steps are explained in detail hereinafter.

Stage (b)

In a preferred embodiment, according to stage (b), organic constituents are removed from at least a portion of the aqueous phase or aqueous phases obtained in stage (a) by stripping.

Stripping is understood to mean the removal of particular volatile constituents from the liquids by the passage of gases (nitrogen, steam, etc.), the constituents mentioned being transferred to the gas phase or discharged from the liquid with the gas phase.

In the context of the present invention the stripping is preferably performed with steam. The stripping is preferably effected in a stripping column, in which case the organic constituents, especially benzene and nitrobenzene, are removed overhead. The stripping column is preferably a tubular device with internals for intensive mass transfer of gaseous and liquid phase. The liquid is preferably passed in countercurrent, i.e. passes through the stripping column against the flow direction of the gas. Corresponding processes and columns are known to those skilled in the art and are described, for example, in W. Meier, Sulzer, Kolonnen für Rektifikation and Absorption [Columns for Rectification and Absorption], in: Technische Rundschau Sulzer, 2 (1979), page 49 ff.

Preferred processes are, for example, stripping in a column, which is preferably filled with random beds of random packings, with structured packings or with mass transfer trays, for example sieve trays, bubble-cap trays, tunnel-cap trays or Thormann trays. The stripping in stage (b) is preferably performed at an absolute pressure of 0.1 to 10 bar, especially 1 to 5 bar, and a temperature of 35 to 180° C., especially at 100 to 160° C.

The condensate which is obtained in the course of stage (b) and comprises the aromatic starting compound and the aromatic nitro compound, and also nonaromatic organic compounds, is subsequently supplied to a phase separator, the organic phase preferably being recycled into the wash in stage (a) and the aqueous phase being fed back to stage (b). In a preferred embodiment, the steam obtained overhead in the stripping column, including the organic constituents, is used as a heat carrier in stage (d), and the condensate obtained is fed to a phase separator, the organic phase preferably being recycled into the wash in stage (a) and the aqueous phase preferably being fed back to stage (b). This preferred embodiment is explained in detail in the context of stage (d).

For safety reasons, error-free function of stage (b) is desirable. Malfunction of the stripping column can be monitored, for example, by redundant safety devices.

Preferably, in stage (b), an alkaline wastewater is obtained, which comprises benzene only in concentrations of at most 30 ppm, especially at most 5 ppm, and nitrobenzene in concentrations of at most 50 ppm, especially at most 20 ppm.

Stage (c)

In the context of the present invention, in the course of stage (c), organic compounds are removed from at least a portion of the aqueous phase or aqueous phases resulting from stage (a) or stage (b) by thermal and/or oxidative degradation.

The removal of organic compounds from at least a portion of the aqueous phase or aqueous phases resulting from stage (a) or stage (b) by thermal degradation is referred to hereinafter as thermolysis. Alternatively, the degradation is effected oxidatively, especially by means of ozone (ozonolysis).

Preferably, in stage (c), the wastewater which is obtained from steps (a) and (b) and is still laden with organic salts of the nitrohydroxyaromatics is heated with exclusion of oxygen to temperatures of 150 to 500° C., preferably of 250 to 350° C., more preferably 250 to 300° C., under elevated pressure. It is also possible to heat the wastewaters under inert gas atmosphere or under an inert gas supply pressure of, for example, 0.1 to 100 bar. Suitable inert gases are, for example, nitrogen and/or argon. According to the temperature and optional inert gas supply pressure, in the course of heating of the wastewaters, preferably absolute pressures in the range from 50 to 350 bar, more preferably 50 to 200 bar, most preferably 70 to 130 bar, are established. The heating of the alkaline wastewater and thermal pressure decomposition of the nitrophenols is effected typically for 5 to 120 min, preferably 20 to 45 min.

The wastewater is thermalized in pressure vessels at a temperature of 150° C. to 350° C., preferably 250° C. to 300° C., a pressure of 10 bar to 200 bar, preferably 70 bar to 150 bar, and a pH of the wastewater of 8 to 14, preferably 9 to 13.

The pressure vessels used may be all pressure vessels which are known from the prior art and are designed for the abovementioned temperatures and pressures. For a continuous process regime, suitable examples are tubular reactors and autoclaves connected in a cascade.

In a preferred configuration, the wastewater is conveyed with a pump through a heat exchanger in which it is preheated, for example, to 280° C. Subsequently, the preheated wastewater is heated to 300° C. by direct injection of 100 bar steam or by indirect heating. After a residence time of 20 min to 60 min, the reaction solution is cooled in countercurrent with the feed, and decompressed.

For continuous configuration of the process, preference is given to using a tubular reactor in which the flow of the liquid is adjusted such that there is no backmixing.

Preferably, stage (c) is performed as thermolysis in the absence of an inert gas at an absolute pressure of 50 to 350 bar and a temperature of 150 to 500° C.

In an alternative embodiment, organic compounds, especially nitrophenols, are removed from at least a portion of the aqueous phase or aqueous phases resulting from stage (a) or stage (b) by oxidative degradation, preferably by ozonolysis.

Processes for ozonolysis of wastewaters from the nitration of aromatic compounds are likewise known to those skilled in the art. Preference is given to effecting the oxidative degradation by treatment with ozone at 20 to 100° C., a pressure of 1.5 to 10 bar and a pH of 3 to 12. The ozonolysis is preferably performed continuously in a cascade of reactors which are connected in countercurrent. In this way, the ozone is removed so completely from the gas stream that it is usually possible to dispense with a residual ozone destruction. Corresponding processes are described especially in EP 0 378 994 A1, the contents of which are hereby fully incorporated by reference.

After completion of stage (c), the content of nitrophenols in the wastewater is preferably at most 100 ppm, especially at most 30 ppm. The content of ammonia in the wastewater which results from stage (c) is typically from 100 to 3000 ppm, especially from 500 to 1500 ppm. The nitrate content in the wastewater which results from stage (c) is typically from 5 to 500 ppm, especially from 20 to 300 ppm. The nitrite content in the wastewater which results from stage (c) is typically from 200 to 10 000 ppm, especially from 500 to 3000 ppm. The content of organically bound nitrogen (calculated in atomic terms) in the wastewater which results from stage (c) is typically from 5 to 200 ppm, especially from 5 to 40 ppm.

Stage (d)

According to the present invention, stage (d) involves the distillative depletion of ammonia from the aqueous phase or aqueous phases resulting from stage (b) or (c). The aqueous phase(s) can be distilled by processes known per se.

Preference is given to performing the distillation in stage (d) at an absolute pressure of 0.1 to 10 bar, especially 1 to 5 bar, the pressure mentioned being present at the top of the distillation apparatus.

Preference is given to performing the distillative removal of ammonia in stage (d) at a temperature of 80 to 140° C., the temperature mentioned being present at the top of the distillation apparatus.

Preferably, the ammonia content in the aqueous phase after stage (d) is no more than 100 ppm, especially not more than 20 ppm, more preferably not more than 10 ppm.

The distillative depletion of ammonia from the aqueous phase(s) resulting from stage (b) is preferably accomplished at temperatures of 50 to 160° C. and absolute pressures of 0.1 to 10 bar, especially 1 to 5 bar.

The distillative depletion of ammonia can be effected in known apparatus. The evaporation of ammonia is suitably effected in a distillation column. The column may be filled with unstructured packings known to those skilled in the art, for example random beds of random packings, with structured packings or with mass transfer trays, for example sieve trays, bubble-cap trays, tunnel-cap trays or Thormann trays. In a particularly preferred embodiment, unstructured or structured packings and mass transfer trays are combined with one another, so as to achieve an optimal separation effect.

The introduction of heat into the distillation column is preferably effected by an attached evaporator. This allows stage (d) to be integrated into the process in an energetically particularly favorable manner.

An evaporator in process technology is an apparatus for converting a liquid to its vaporous state. For evaporation of the liquid, the supply of thermal energy is required. Evaporators therefore generally consist of a surface through which heat from a heat carrier, preferably a liquid, is transferred to the liquid to be evaporated. Preference is given in the context of the present invention to evaporators which transfer the heat required indirectly (no direct contact between heat carrier and liquid to be evaporated). Corresponding evaporators are known per se to those skilled in the art. Suitable evaporators are especially natural circulation evaporators, forced circulation evaporators, kettle evaporators, steam boilers, falling-film evaporators and thin-film evaporators. Particularly suitable evaporators are those based on a shell and tubes. Particular preference is given to falling-film evaporators.

In a particularly preferred embodiment, stage (d) is coupled for the purposes of heat management to at least one preceding stage, especially stage (b).

The vapor phase resulting from stage (b) is preferably used for indirect heat transfer in stage (d). More preferably, the vapor phase resulting from stage (b) is introduced as a heat carrier into an evaporator in the course of stage (d).

Preferably, the heat carrier, after stage (d), is recycled at least partly into stage (a). In a particularly preferred embodiment, the heat carrier, after stage (d), is subjected to a phase separation to obtain an organic phase and an aqueous phase, the resulting organic phase being recycled into stage (a). The resulting aqueous phase is preferably fed to stage (b).

The wastewater which is obtainable by the process according to the invention and has been freed completely or partially of ammonia can be fed directly, i.e. without further separation steps, to a biological wastewater treatment, especially a water treatment plant. The ammonia-comprising top product obtained here is preferably condensed by methods known per se to those skilled in the art, and is preferably partly recycled as a condensate return stream into the distillation column within stage (d) and partly sent to a further workup, preferably an incineration. Uncondensed constituents can be supplied to a further offgas treatment.

Stage (e)

In the context of stage (e), at least a portion of the aqueous phase resulting from stage (d) is preferably sent to a biological wastewater treatment stage.

Corresponding processes for biological wastewater treatment are likewise known per se to those skilled in the art and are described in detail, for example, in Ullmann's Encyclopedia of Industrial Chemistry 7th edition ("Waste Water" Chapter), 2005 Wiley-VCH Verlag GmbH & Co. KGaA, Weinheim.

EXAMPLES

Example 1

Stage a1, substep 1: 21 t/h of crude nitrobenzene from the nitration of benzene, comprising 1000 ppm by weight of picric acid and 2300 pp by weight of dinitrophenol, were admixed with 0.19 t/h of 25% sodium hydroxide solution and the aqueous phase from stage a1, substep 2, and mixed intensively in a stirred tank at 130 min$^{-1}$.

Stage a1, substep 2: after subsequent phase separation in a downstream phase separation apparatus, the organic phase from stage a1, substep 1, is admixed with 8 t/h of NaOH-alkalized condensate from the vacuum distillation of a sulphuric acid concentration step and 0.001% by weight of demulsifier D1, based on the weight of nitrobenzene, and mixed again intensively at 100 min$^{-1}$. After the phase separation, the aqueous phase was recycled into stage a1, substep 1. The organic phase was supplied to stage a2. The aqueous phase from stage a1, substep 2, comprised 6000 ppm by weight of nitrophenoxides.

Stage a2: The organic phase from stage a1, substep 2, was admixed with 6 t/h of wastewater from aniline production (0.2% by weight of mononitrobenzene and 200 ppm of ammonia, pH 9) and likewise 0.001% by weight of demulsifier D1, and mixed in a stirred tank at 90 min$^{-1}$. After subsequent phase separation in a downstream phase separation apparatus, 21 t/h of mononitrobenzene free of nitrophenols (content below the detection limit) were obtained. The wastewater from stage a2 comprised less than 10 ppm by weight of nitrophenoxides. A thermolytic or ozonolytic wastewater treatment of the aqueous phase can be omitted.

The demulsifier D1 used was an amphiphilic anionic copolymer comprising olefin and maleic acid units (Na salt) as a 25% by weight aqueous solution with a pH to DIN 19268 at 23° C. of 11, an iodine number to DIN EN 1557 at 23° C. of 2 and a K value to ISO 1628-1 as a 1% by weight solution in dist. water of 35. The sodium maleate content, calculated as maleic acid, in the copolymer, determined by means of HPLC, was 0.3% by weight.

The water content of the organic phases in stage a1, substep 2, was 0.4% by weight (at 50° C.); the phase interfaces were sharp in all cases.

Comparative Example 2

The same experiment as in the example was conducted without demulsifier. In this case, a sharp phase interface was not achieved in all stages; the water content in the organic phases of wash stage a1 rose up to 8.5%.

The invention claimed is:
1. A process for purifying crude aromatic nitro compounds which originate from the nitration of aromatic compounds, comprising the single or multiple performance of the following wash stage (a):
   (a) contacting the crude aromatic nitro compound (N-in) with an aqueous phase (W-in) and then separating the phases to obtain an organic phase (N-res) and an aqueous phase (W-res), wherein at least one demulsifier (D) is present in one or more of the wash stages (a), wherein the demulsifier (D) is an amphiphilic compound.

2. The process according to claim 1, wherein the demulsifier (D) is present in an amount of 1 to 100 ppm, based on the weight of the aqueous phase (W-in).

3. The process according to claim 1, wherein the demulsifier (D) is an anionic copolymer.

4. The process according to claim 1, wherein the demulsifier (D) is a copolymer comprising carboxylate groups.

5. The process according to claim 1, wherein the demulsifier (D) is a copolymer comprising maleic acid units.

6. The process according to claim 1, wherein the demulsifier (D) is a copolymer comprising maleic acid units and olefin units.

7. The process according to claim 1, wherein wash stage (a) is performed at least twice and comprises the following wash stages (a1) and (a2), where each of stages (a1) and (a2) may be performed once or more than once in succession:
 (a1) contacting the crude aromatic nitro compound (N1-in) with a first aqueous phase (W1-in) comprising at least one base (B) and then separating the phases to obtain an organic phase (N1-res) and an aqueous phase (W1-res); and then
 (a2) contacting the organic phase (N1-res) obtained in stage (a1) with a second aqueous phase (W2-in) and then separating the phases to obtain a purified organic phase (N2-res) and at least one aqueous phase (W2-res), the aqueous phase used (W2-in) having a pH of 6 to 9.

8. The process according to claim 7, wherein the pH of the first aqueous phase (W1-in) comprising at least one base (B) is from 10 to 14.

9. The process according to claim 7, wherein the first aqueous phase (W1-in) comprises sodium hydroxide as the base (B).

10. The process according to claim 7, wherein stage (a1) is performed in at least two repetitions and the aqueous phase (W1-in) used is conducted in countercurrent to the organic phase (N1-in) in the course of wash stage (a1).

11. The process according to claim 7, wherein stage (a2) is performed in two repetitions and the aqueous phase (W2-in) used is conducted in countercurrent to the organic phase (N2-in) in the course of wash stage (a2).

12. The process according to claim 7, wherein the aqueous phase (W1-res) is subjected to the following further workup stages:
 (b) optional removal of organic constituents from at least a portion of the aqueous phase (W1-res) obtained in stage (a) by stripping,
 (c) removal of organic compounds from at least a portion of the aqueous phase (W1-res) resulting from stage (a) or stage (b) by thermal and/or oxidative degradation,
 (d) distillative depletion of ammonia from at least a portion of the aqueous phase resulting from stage (c), and
 (e) optional supply of at least a portion of the aqueous phase resulting from stage (d) to a biological wastewater treatment.

13. The process according to claim 7, wherein the aqueous phase (W2-res) is subjected to the following further workup steps:
 (b) optional removal of organic constituents from at least a portion of the aqueous phase (W2-res) obtained in stage (a) by stripping,
 (d) distillative depletion of ammonia from at least a portion of the aqueous phase(s) resulting from stage (c), and
 (e) optional supply of at least a portion of the aqueous phase resulting from stage (d) to a biological wastewater treatment.

14. The process according to claim 7, wherein the aqueous phase (W2-in) used is a wastewater from a different production process which does not comprise any nitrophenols.

15. The process according to claim 7, wherein the aqueous phase (W2-in) used is a wastewater which is obtained from the hydrogenation of mononitrobenzene.

16. The process according to claim 7, wherein a demulsifier (D) is present in stage (a1).

17. The process according to claim 7, wherein a demulsifier (D) is present in stage (a2).

18. The process according to claim 12, wherein said stripping is with steam.

19. The process according to claim 13, wherein said stripping is with steam.

* * * * *